(12) United States Patent
Caron (10) Patent No.: US 8,058,885 B2
(45) Date of Patent: Nov. 15, 2011

(54) POROUS MEDIUM ELECTRICAL CONDUCTIVITY SENSOR

(75) Inventor: Jean Caron, Saint-Romuald (CA)

(73) Assignee: Hortau Inc., Quebec (CA)

( * ) Notice: Subject to any disclaimer, the term of this patent is extended or adjusted under 35 U.S.C. 154(b) by 393 days.

(21) Appl. No.: 12/446,505

(22) PCT Filed: Nov. 1, 2007

(86) PCT No.: PCT/CA2007/001975
§ 371 (c)(1),
(2), (4) Date: Apr. 21, 2009

(87) PCT Pub. No.: WO2008/052351
PCT Pub. Date: May 8, 2008

(65) Prior Publication Data
US 2010/0194411 A1    Aug. 5, 2010

Related U.S. Application Data

(60) Provisional application No. 60/856,312, filed on Nov. 3, 2006.

(51) Int. Cl.
*G01R 27/08* (2006.01)

(52) U.S. Cl. .................................... 324/694; 324/453

(58) Field of Classification Search .............. 324/694, 324/453
See application file for complete search history.

(56) References Cited

U.S. PATENT DOCUMENTS

| | | |
|---|---|---|
| 2,941,174 A | 6/1960 | Richards |
| 3,181,098 A | 4/1965 | Richards |
| 3,430,486 A | 3/1969 | Richards |
| 3,508,148 A | 4/1970 | Enfield |
| 3,782,179 A | 1/1974 | Richards |
| 4,137,931 A | 2/1979 | Hasenbeck |
| 4,545,396 A | 10/1985 | Miller et al. |
| 4,561,293 A | 12/1985 | Richards |
| 4,646,000 A | 2/1987 | Wills |
| 5,179,347 A | 1/1993 | Hawkins |
| 5,898,310 A | 4/1999 | Liu |
| 6,842,018 B2 | 1/2005 | McIntosh |
| 2003/0011386 A1 * | 1/2003 | Xie et al. ................... 324/694 |

FOREIGN PATENT DOCUMENTS

WO    2004/112467    12/2004

* cited by examiner

*Primary Examiner* — Vincent Q Nguyen
(74) *Attorney, Agent, or Firm* — Robic (57) ABSTRACT

There is provided a sensor for measuring a quantity, such as the salinity, of the soil solution without requiring continuous calibration. The sensor is based on a porous material which automatically fills up and saturates when the soil is rewet and drains when the soil dries out from plant uptake or from air drying, then being filled up with a solution representative of the quantity to be measured in the soil during plant growth.

24 Claims, 5 Drawing Sheets

POROUS MEDIUM ELECTRICAL CONDUCTIVITY SENSOR

CROSS-REFERENCE TO RELATED APPLICATIONS

This application claims priority of U.S. provisional patent application 60/856,312 filed Nov. 3, 2006 and of PCT patent application WO 2008/052351 filed Nov. 1, 2007, the specifications of which being hereby incorporated by reference.

TECHNICAL FIELD

The invention relates to a sensor for measuring the electrical conductivity of a porous medium such as soil for growing plants. More particularly, the measured electrical conductivity is representative of the salinity of a sample of the liquid phase of the porous medium.

BACKGROUND OF THE ART

Plant growth is controlled to a large extent by water availability from the surrounding soil to the plant. Plant available water in the surrounding soil depends on the pore sizes and the surfaces offered by the mineral component of the soil. The two components generate soil matrix suction forces, also called matrix potential.

Because plant root cells have a semi-permeable membrane at their periphery, solutes can accumulate outside of the root and generate a second potential, the osmotic potential, which affects the plant growth. Solute content of the soil, or soil salinity, is linked to the electrical conductivity of the soil. For irrigated lands in which fertilizers are added (fertigation), like greenhouse and nursery production, for soils with high salt content or for irrigated lands using a large amount of fertilizers, salts built up can have detrimental effects on plant growth and therefore, electrical conductivity is regularly monitored. If needed, excess solution is applied to leach excess salts to the environment, therefore creating environmental detrimental effects. Because of the difficulty of measuring the soil solution electrical conductivity, leaching is often carrying out in excess, therefore increasing the risk of groundwater pollution by excess fertilizers or pesticides.

Therefore, numerous efforts have been carried out to measure electrical conductivity in the soil solution to help monitoring irrigation and leaching, and to optimize plant growth. However, the technology proposed so far is based on a Wenner arrangement, i.e. an arrangement of four electrodes, inserted directly into the soil for electrical conductivity measurement. Such a procedure measures the apparent electrical conductivity of the soil solution. The apparent electrical conductivity measurement is also dependent on the soil water content, soil structure and solid phase electrical properties of the soil.

U.S. Pat. No. 3,508,148 to Enfield discloses a sensor for measuring the electrical conductivity in a soil. The sensor uses a porous glass plate with pores having a diameter in the range of ten to one hundred angstrom units. A plate electrode is placed on one side of the porous glass plate and a grid electrode is placed on the opposite side. The openings of the grid provide the exposure of the porous glass to the soil wherein it is inserted, in order to allow the porous glass plate to draw the water solution of the soil in its pores by capillarity. The electrical conductivity of the porous glass plate is measured using the electrodes. As the salinity of the soil varies, the solution drawn in the pores of the porous glass plate stabilizes to the salinity of the soil by diffusion. Consequently, the time required to reach a steady state condition in the porous glass is about eight hours which is quite long for plant growth applications, since soil may be irrigated few times a day.

Furthermore, water in a soil, or a growing medium, comprises drainage water, plant available water and plant non available water. Plant non available water corresponds to bound water and available water corresponds to water that is contained in the soil and that can be drawn by plants or growing crops. Drainage water is the excess in water that drains out of the growing medium. The salinity to be monitored in plant growth applications corresponds to the salinity of the plant available water, i.e. the growing soil's solution.

In Enfield's sensor, because of the selected pore size, the porous glass does not discriminate between plant available water, plant unavailable water and both available and unavailable water are sampled by the porous medium.

SUMMARY

There is provided a sensor for measuring a quantity, such as the salinity or a concentration of a component of the soil liquid solution, of the soil solution without requiring continuous calibration. The sensor is based on a porous material which automatically fills up and saturates when the soil is rewet and drains when the soil dries out from plant uptake or from air drying, then being filled up with a solution representative of the quantity to be measured in the soil during plant growth.

One aspect of the invention provides a sensor for measuring a concentration in a liquid solution in a porous medium. The sensor comprises a porous material and an electrical transducer for measuring an electrical quantity in the porous material. The electrical quantity is representative of the concentration in the liquid solution. The porous material has pores with a substantially uniform pore size. When the porous material is at least partly inserted in the porous medium, the pores are substantially saturated with the liquid solution when the porous medium contains the liquid solution in a content above a threshold value and the pores are substantially empty from the liquid solution when the content is below the threshold value.

Another aspect of the invention provides a sensor for measuring a parameter in a liquid solution in a porous medium. The sensor comprises a porous material tip to be at least partly inserted in the porous medium, and an electrical transducer for measuring an electrical quantity in the porous material tip. The electrical quantity is indicative of the parameter of the liquid solution. The porous material tip has pores of substantially uniform size, the size being such that the porous material tip is to be substantially saturated in the liquid solution when the porous medium contains plant available water and such that the porous material tip is to be substantially free when the porous medium contains substantially no plant available water.

Still another aspect of the invention provides a method for measuring a parameter in a porous medium using a porous material tip having pores having a pore size. The porous material tip is to be inserted in the porous medium. The pore size is determined such that, when there is plant available water in the porous medium, pores are substantially saturated with the plant available water and such that, when the porous medium is substantially free of available water, the pores are free of the available water. A porous material tip having substantially uniform pores of the pore size is provided. The porous material tip has substantially no electrical conductivity when the pores are empty. The porous material tip is inserted in the porous medium. An electrical quantity is measured in the porous material tip. The electrical quantity is indicative of the parameter. A measurement of the parameter obtained from the measured electrical quantity is outputted.

BRIEF DESCRIPTION OF THE DRAWINGS

FIG. 6 is a cross-sectional view of another salinity sensor wherein the electrical conductivity meter has four ring electrodes in a Wenner arrangement;

FIG. 7 shows another salinity sensor wherein the porous material tip is mostly external to the housing and comprises FIG. 7A and FIG. 7B which are respectively a partial perspective view and a partial cross-section view taken along lines 7-7 of FIG. 7A;

FIG. 8 is a schematic block diagram showing a modular salinity sensor installed in a porous medium.

It will be noted that throughout the appended drawings, like features are identified by like reference numerals.

DETAILED DESCRIPTION

Figure 1:
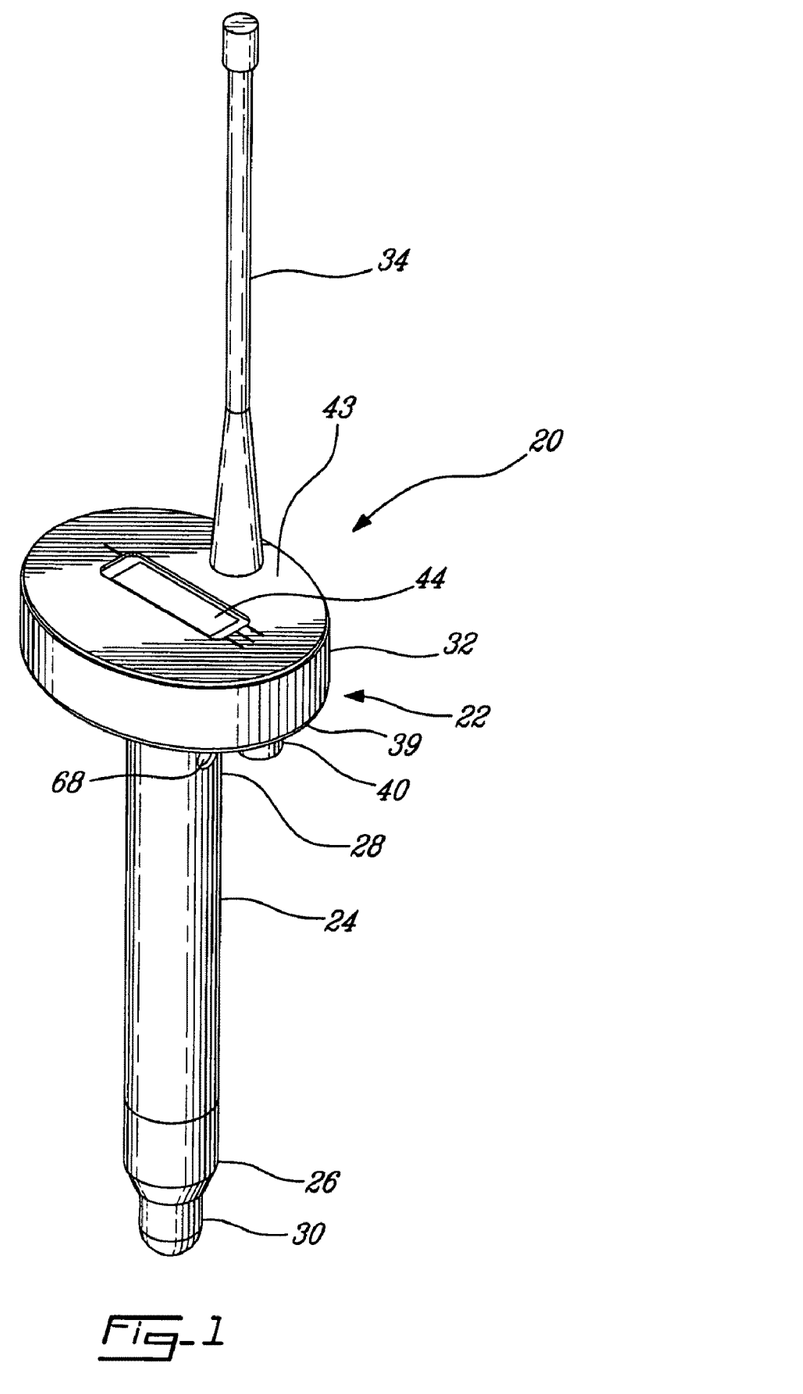
FIG. 1 is a perspective view of a salinity sensor.

FIG. 1 illustrates a salinity sensor 10 for measuring the salinity of a solution in a porous medium such as earthen soil, greenhouse soil or any growing medium used in horticulture, without requiring continuous in-field calibration to compensate for variation of the water content, the structure or the solid phase electrical conductivity of the porous medium. The sensor 10 is calibrated once in factory and does not typically require any periodic calibration in the field.

Figure 3:
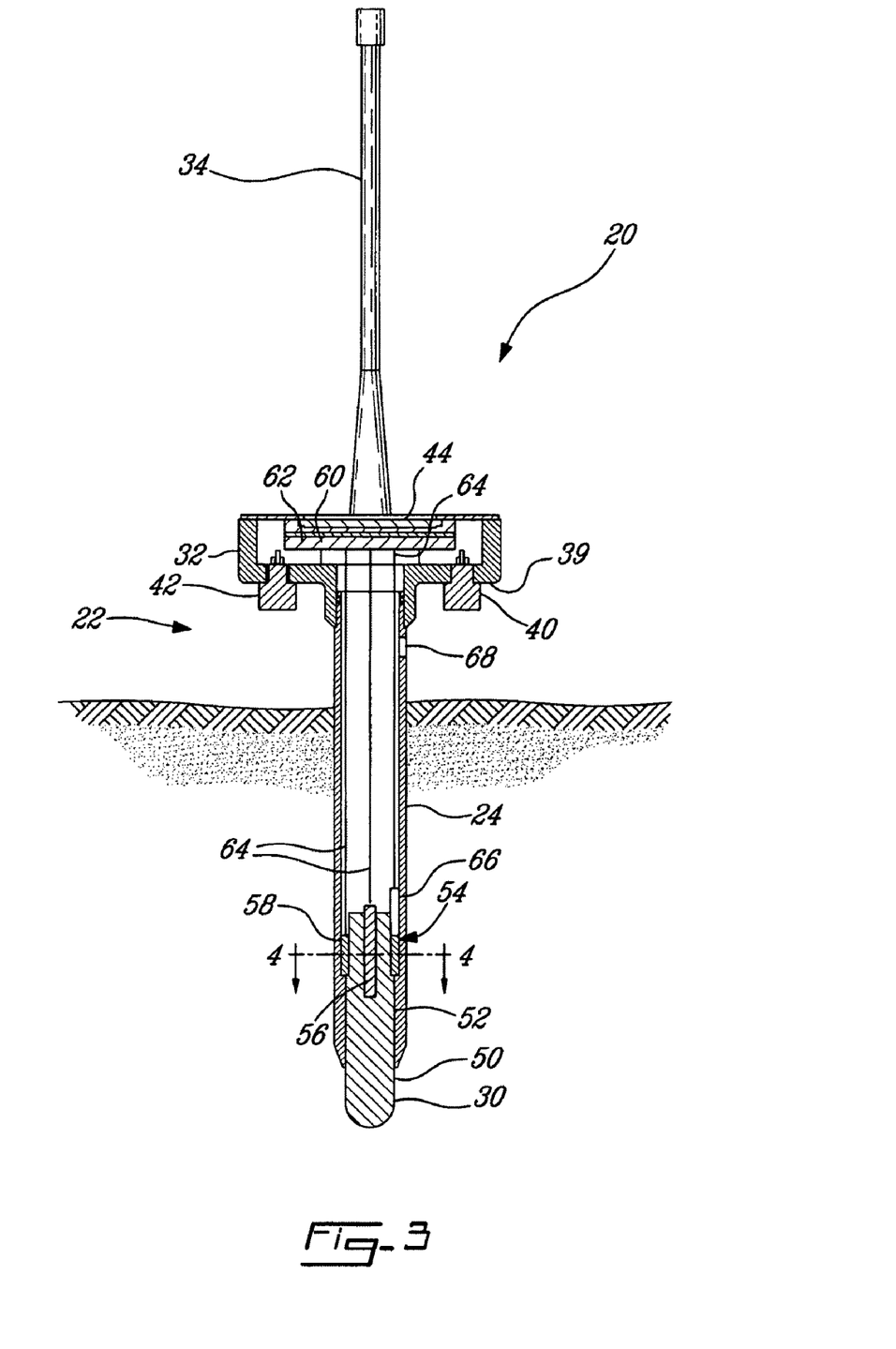
FIG. 3 is a cross-sectional view taken along lines 3-3 of FIG. 2, wherein the salinity sensor is inserted in a porous medium.

The salinity sensor 20 has a body 22 for insertion in the porous medium to be sampled and which includes a tubular housing 24 with a lower end 26 and an upper end 28 and a porous material tip 30, and a head 32 with an antenna 34 which extends out of the porous medium when the tubular housing 24 and the porous material tip 30 are inserted therein. The porous material tip 30 is mounted to the lower end 26 of the tubular housing 24. The porous material tip 30 has a first section which extends in the tubular housing 24 and a second section which is in direct contact with the porous medium when inserted therein as shown in FIG. 3, as will be described in more details below.

The head 32 of the salinity sensor 20 is mounted to the upper end 28 of the tubular housing 24. The antenna 34 is mounted to the head 32 of the salinity sensor 20 for wirelessly transmitting the monitored salinity to a remote data logger.

The lower face 39 of the head 32 has two connectors 40, 42 (see FIG. 3) extending downwardly therefrom. The purpose of these connectors 40, 42 will be described in more details below.

The upper face 43 of the head 32 includes an electronic dial 44. The electronic dial 44 can display, amongst others, the current salinity measurement and, optionally, a temperature measurement.

Figure 2:
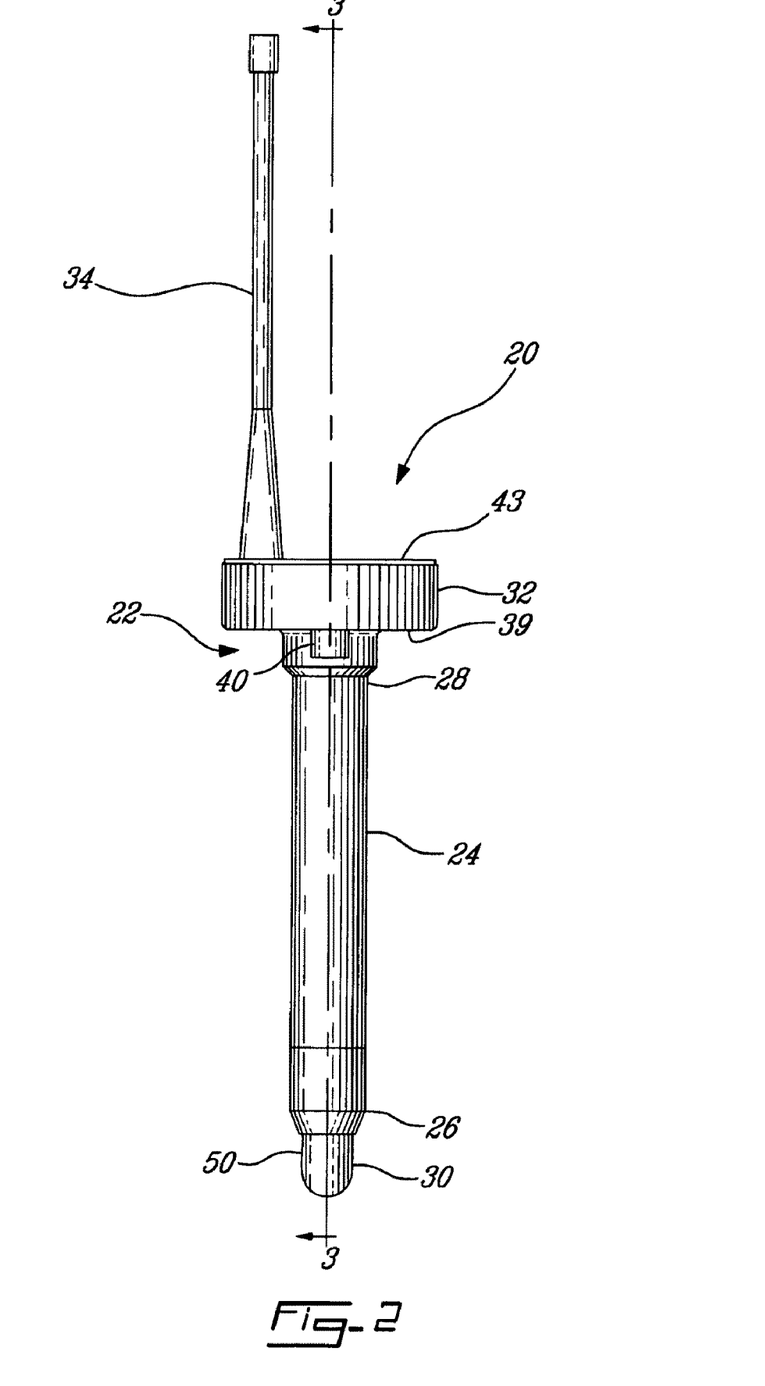
FIG. 2 is a side elevation view of the salinity sensor of FIG. 1.
Figure 4:
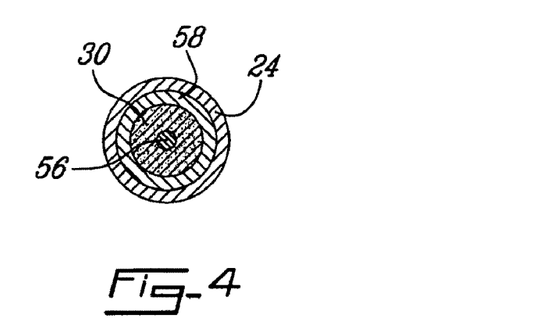
FIG. 4 is a cross-sectional view taken along lines 4-4 of FIG. 3.

Referring now to FIGS. 2 to 4 simultaneously, the internal structure of the salinity sensor 20 will be described in more details. The sensor 20 includes a porous material tip 30 having a specific pore size. The porous material tip 30 is a substantially cylindrical body of porous material and has an external section 50 extending outside the tubular housing 24 from the lower end 26 and an enclosed section 52 located inside the tubular housing 24. When the salinity sensor 20 is inserted in the porous medium, the porous material tip 30 is in contact with the porous medium and draws water by capillarity from the porous medium through the external section 50 and to the enclosed section 52 of the porous material tip 30, and consequently samples the liquid phase solution in the porous medium. An electrical conductivity measurement is carried out within the enclosed section 52 of the porous material tip 30 using a transducer, namely an electrical conductivity meter 54. As will be described herein below, the measured electrical conductivity is representative of the salinity of the solution of the porous medium. To avoid air entrapment in the tubular housing 24, a gas exchange opening 68 may be provided on the tubular housing 24 near its upper end 28 for allowing gas pressure inside the tubular housing to equilibrate with the air surrounding the sensor 20. In this case, the air exchange opening extends above the porous medium when the sensor 20 is inserted therein.

The electrical conductivity meter 54 comprises two electrodes 56, 58 and an electrical conductivity measuring circuit 60. The electrical conductivity measuring circuit 60 is included in an electrical circuit board 62 located in the head 32 of the salinity sensor 20. A first electrode, a straight electrode 56, is inserted in the porous material tip 30 along its middle axis. A second electrode, a ring electrode 58, surrounds the porous material tip 30, is in direct contact with its peripheral surface and is located between the porous material tip 30 and the tubular housing 24. The two electrodes 56, 58 are connected to the electrical conductivity measuring circuit 60 located in the head 32 of the salinity sensor 20, using electrical connections 64.

In order to measure the electrical conductivity of the porous material tip 30, an alternating voltage is applied to the electrodes 56, 58 and the electrical current consequently flowing in the porous material tip 30 is measured using the electrical conductivity measuring circuit 60. According to the Ohm's law, the electrical conductivity of the porous material tip 30 is found. As will be explained herein below, due to the properties of the porous material tip 30, the measured electrical conductivity is a function of the salinity of the liquid phase solution of the porous medium and is independent of the water content and the properties of the solid phase of the porous medium. The electrical conductivity measurement is thus converted into a salinity measurement according to a predetermined in-factory calibration of the salinity sensor 20.

The salinity monitored by the salinity sensor 20 is displayed on the electronic dial 44 and is also transmitted to a remote data logger (not shown) which records the data received from the salinity sensor 20. The data is wirelessly transmitted through the antenna 34. Alternatively, the data can be read through the connector 42.

The other connector 40 is used to connect the salinity sensor 20 to a power supply (not shown). The power supply may provide power to the salinity sensor 20 and, more particularly, to the electric circuitry including the electronic circuit board 62. In one embodiment, the salinity sensor 20 is self-powered using an internal power source and/or a solar battery.

A temperature measuring device 66, in this case a thermistor, is provided in the surroundings of the porous material tip 30 and in electrical connection with the electrical circuit board 62 using the electrical connections 64. The temperature measuring device 66 is used to compensate for the predetermined variation in temperature of the relation between the electrical conductivity of the porous medium and the salinity of the sampled liquid phase solution. The temperature measuring device 66 may be an independent thermistor or thermocouple for example. Temperature compensation is achieved using this independent temperature reading. The independent temperature reading is provided to the electrical circuit board 62 which directly performs a temperature compensation of the salinity measurement.

The porous material tip 30 is a material having a stable structure and pores of a substantially uniform size. The pore size is designed such that the porous material tip 30 is saturated in water over the useful range of soil matrix potential of the sensor 20, i.e. a range over which the porous medium is wet and water is available for plants and over which the salinity of the porous medium is to be measured; but such that the porous material tip 30 drains when the porous medium dries out from plant uptake and/or from air drying, i.e., when the content of plant available water in the porous medium is significantly low and rewetting becomes necessary. Draining of the porous material tip 30 reinitializes the sensor 20 and the porous material tip 30 consequently draws a completely new solution sample each time the porous medium is rewetted and a critical suction is reached, and quickly stabilizes upon wetting of the porous medium.

Figure 5:
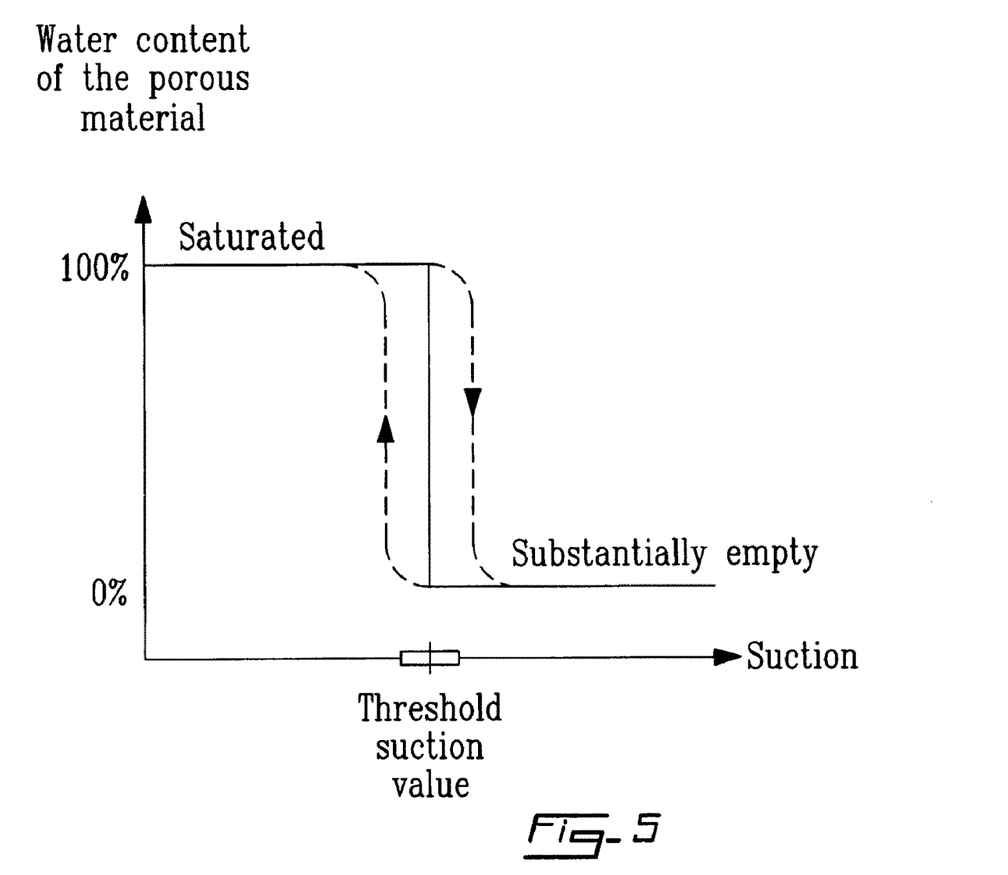
FIG. 5 is a graph showing the water content of the porous material used in the salinity sensor as the matrix potential of the porous medium varies.

The electrical conductivity of the liquid phase of the porous medium is measured in the porous material tip 30. The liquid phase fills the pores and the apparent electrical conductivity of the filled porous material tip 30 is measured and converted into a salinity measurement. The electrical conductivity of a porous material containing a liquid, such as the porous material tip 30, is given by the following equation:

$$\sigma_b = \theta \tau \sigma_l + \sigma_s$$

where $\sigma_b$ is the apparent electrical conductivity of the porous material, $\sigma_l$ is the electrical conductivity of the liquid phase, $\sigma_s$ is the electrical conductivity of the solid phase, $\theta$ is the fluid content of the porous material and $\tau$ is the electrical tortuosity factor, i.e., the ratio of the real to the apparent length for electron movement in a porous material. As will be described hereinabove in reference to FIG. 5, the porous material tip 30 is characterized by a unique water content upon wetting, i.e., $\theta$ is constant. Furthermore, it is made of a material having a stable structure, therefore providing a constant electrical tortuosity factor $\tau$, and having no electrical conductivity when the pores are empty of water solution or filled with pure water, i.e., $\sigma_s$ is null. Because of these characteristics, the apparent electrical conductivity $\sigma_b$ in the porous material tip 30 is independent of the structure, the water content and the electrical conductivity of the solid phase of the sampled porous medium. As long as the sensor is operated over a predetermined useful range of matrix potential of the sampled porous medium, such that the pores of the porous material tip 30 are saturated, the electrical conductivity of the porous material tip 30 is a unique function of the salinity of the liquid phase of the sampled porous medium. This implies that, over the predetermined range of matrix potential of the porous medium, there exists a single relationship between the electrical conductivity of porous material tip 30 and the salinity of the sampled liquid phase of the porous medium. Furthermore, the porous material tip 30 has no memory as it is drained and refilled, because ions in the liquid phase of the porous medium are not sorbed on the pore surface of the porous material (no permanent or variable electrical charges).

In one embodiment, the porous material is a porous glass made by sintering glass powder. Pure silica or slightly altered silica powder may be used, for instance. In order to ensure a uniform pore size throughout the porous material, the glass powder is screened to obtain a glass powder of unique solid particle size. The glass powder is then sintered with controlled compaction and cooking temperature parameters such that a substantially unique and appropriate pore size and an appropriate porosity are obtained. Glass beads can be typically fritted in a furnace at temperature between 500 to 800° C. for about fifteen minutes to one hour and a half, and then cooled down. The specific size of the glass beads should be selected to obtain the pore size on the fritted matrix. A porous plastic material made by plastic powder sintering, a fiber glass material, or any other solid and non-conductive porous material could alternatively be used as a porous material.

If necessary, the sensor 20 may be recalibrated in the field or in factory using one solution of known electrical conductivity.

Now referring to FIG. 5, the water content of the porous material tip is shown as a function of the suction. The characteristics of the porous material tip 30, more particularly, the pore size, the pore size variance and the porosity, determine the water content response of the porous material tip 30. The substantially step function is mostly provided by the unique pore size. The porous material is characterized by a critical suction below which the porous material tip 30 is substantially saturated and above which the porous material tip 30 is substantially empty of water solution. It is noted that the suction corresponds to the absolute value of the matrix potential of the porous medium.

When the probe is inserted into a porous medium, the porous material tip 30 equilibrates to the matrix potential of the porous medium. If the porous medium is at a suction greater than the critical suction, as a result of plant water uptake in the porous medium for example, the porous material equilibrates with the porous medium and therefore empties of water. If water is provided by irrigation or rainfall, the suction of the porous medium consequently decreases below the critical suction and the porous material tip 30, as a result of a new equilibrium of the porous material tip 30 with the porous medium, draws water from the porous medium into the porous material tip 30. Due to a the unique pore size, the porous material tip abruptly saturates when the suction drops below the critical suction.

The critical suction substantially corresponds to the limit where the porous medium contains no or very low plant available water. The porous material is substantially empty when there is no available water and is substantially saturated when there is a significant amount of available water. As described hereinabove, consequently, the water content of the porous material tip 30 is substantially independent of the matrix potential and the water content of the porous medium when the porous medium contains plant available water (the suction is below the critical suction), and the porous material tip 30 drains of porous medium solution as the porous medium dries out of plant available water. The porous material tip 30 is thus initialized periodically during a normal irrigation cycle of the porous medium. As the porous medium is being watered, the critical suction is reached and the pores of the porous material tip 30 fill and saturate with the porous medium liquid phase solution. The porous material thus draws a new solution sample each time the porous medium is being watered. The stabilization of the solution sampled by the porous material tip is thus made by convective flow, as opposed to diffusion, a process much faster than diffusion only. The porous material is consequently memory free and stabilizes in few minutes.

Ideally, the water content response curve has a step shape (solid line of FIG. 5), i.e. the pores fill or drain abruptly when the suction crosses a threshold suction value. As shown in FIG. 5 (dashed line), in reality, the pores fill and drain over a threshold suction range surrounding the threshold suction value An hysteresis effect may also be observed. In this latter case, the threshold suction value is slightly different when the pores drain than when they fill. A small hysteresis effect should not have any substantial effect on the salinity measurement but it should nonetheless be limited as possible. Providing a gas exchange opening 68 on the tubular housing 24 helps in reducing such an hysteresis due to air entrapment pressure that could otherwise build up in the tubular housing 24. As will be discussed hereinbelow, the positioning of the porous material tip such that straight electrode is disposed horizontally in the porous medium may also help in reducing the hysteresis effect.

The pore size is designed such that pores empty and fill over the range of matrix potential characteristic of the matrix potentials maintained in the porous medium during plant growth, according to typical irrigation set points used in fields or in greenhouses. The porous material tip 30 automatically fills up when the soil is rewet and drains when the soil dries from plant uptake and/or from air drying. In a typical irrigation cycle of the porous medium, the salinity is monitored when the porous medium is wet and over a substantially large range of the porous medium water content. As the porous medium dries out and the water matrix potential goes beyond the given critical suction determined by the characteristics of the porous material tip 30, the porous material tip 30 drains and is consequently initialized. The empty range of the porous material tip 30 corresponds to a critical water content of the porous medium where watering is nearly required because substantially no more water is available for the plants. As the porous medium is being watered, the matrix potential of the porous medium steps below the critical suction and a new solution sample is drawn by the porous material tip 30. The porous material tip 30 thus periodically refills with a solution currently representative of the salinity existing in the soil during plant growth. For example, in greenhouse and nursery growing medium applications, the suitable pore size should be found between 70 to 350 µm. For use in mineral soils, the suitable pore size should be found between 2 and 20 µm. A suitable porosity of the porous material tip is typically between about 30 and 40%. More generally, for various porous media and set points, the specific suitable pore size should be found somewhere between 1 and 1000 µm. Experimental tests have been performed using a porous material tip with a standard deviation of its pore size of about 10%. It is noted that a standard deviation below 15% should generally be suitable. Lower standard deviations are nonetheless desirable.

A wet porous medium comprises drainage water, plant available water and plant unavailable water. The salinity to be monitored in plant growth applications corresponds to the salinity of the plant available water. The critical suction is thus selected such that, over the useful range of matrix potential of the porous medium, the suction of the porous material tip 30 matches the matrix potential of the porous medium such that the solution sampled by the porous material tip 30 corresponds to plant available water, non-available water not being sampled.

The critical suction value depends on the characteristics of the porous material and more particularly on the size of the pores and should be adapted to the range of matrix potential of the soil in a given application of the salinity sensor 20. The critical suction value should thus be adapted to the type of soil used in a particular application. Properties of the various types of soils are known in the art and are provided in Verdonck, O. F., Cappaert, T. M. and De Boodt, M. F. 1978. Physical characterization of horticultural substrates. Acta Hort. 82: 191-200. (artificial growing media) and in Koorevaar, P, G. Menelik et C. Dirksen. Elements of soil physics, Elsevier, 1983, ISBN 0-444-42242, Pays-Bas, p. 84-85. (mineral soils). For a given porous medium to be sampled, the specific appropriate pore size and porosity resulting in the required critical suction are typically found by experimental trials and errors.

It is noted that the salinity sensor may have different shapes. For example, a rectangular block of porous material or a plate of porous material may be used as a tip. For example, two plate electrodes located on opposite sides of the porous material may then be used for measuring the electrical conductivity. An electrically isolating casing could then be used for preventing an electrical current between the two electrodes to circulate outside the porous material.

It is also noted that the parameter of the liquid phase solution measured by the sensor may vary. For example, the electrical conductivity only, rather than the salinity, of the liquid phase solution may be measured and outputted by the sensor. Furthermore, the electrical conductivity meter described herein measures the electrical conductivity in the porous material tip but it is noted that it may be replaced by another electrical transducer measuring a different electrical quantity in other applications. For example, an electrical current or an electrical potential can be measured. For example, a chemically selective transducer comprising selective electrodes may be used, the electrical transducer measuring an electrical potential at the electrodes. A sensor for measuring the pH of the liquid phase solution can be constructed using an $H^+$-selective transducer, for example, which measures the concentration of $H^+$ in the liquid phase solution. The concentration in other ions or in other components in solution in the liquid phase solution can also be measured. For example, nitrate sensors for measuring the concentration of nitrate in the solution can be constructed using nitrate-selective electrodes, or phosphate sensors for measuring the phosphate concentration can be constructed using phosphate-selective electrodes.

Figures 6, 7A:
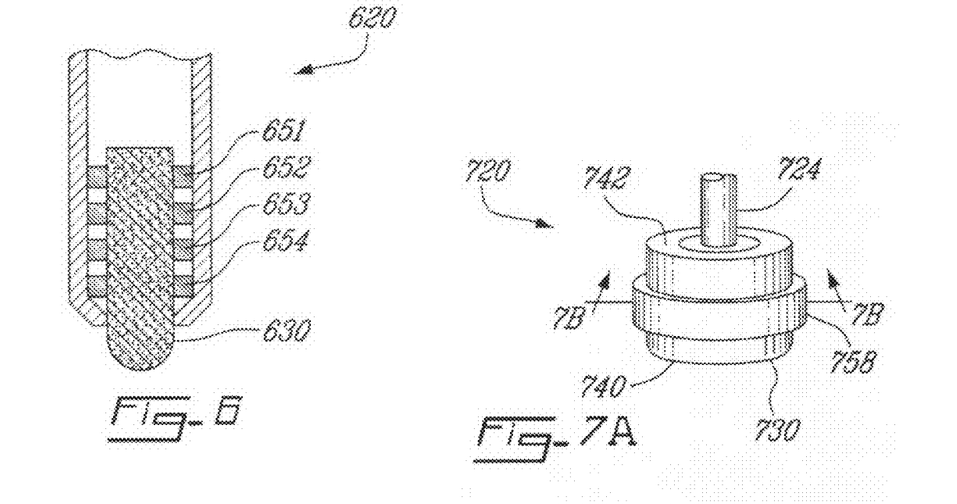
Figures 7B, 8:
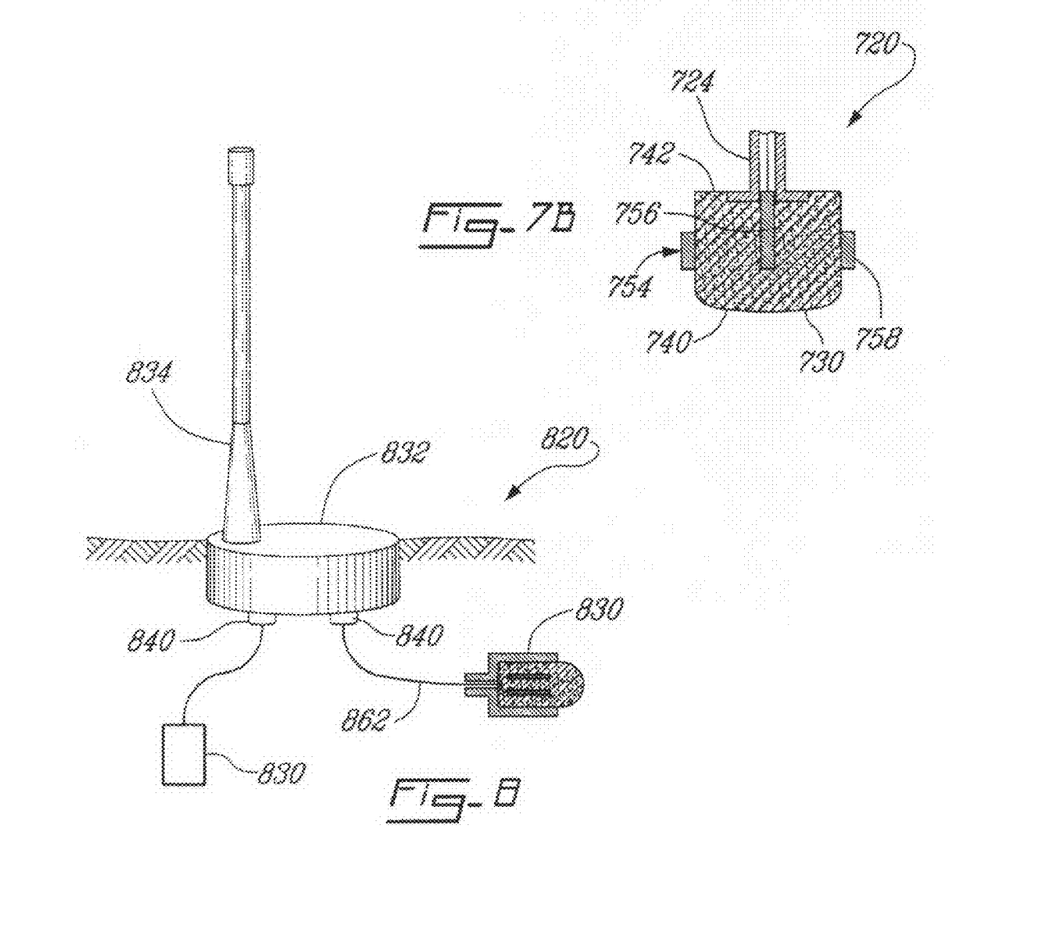

FIGS. 6 to 8 show other possible embodiments of the salinity sensor. The embodiment of FIG. 6 is in all point similar to the one of FIGS. 2 to 4, except that a four-electrode Wenner arrangement is used instead of the two-electrode arrangement of FIGS. 2 to 4. The Wenner arrangement shown in FIG. 6 has four parallel ring electrodes 651, 652, 653, 654 stacked vertically and each in electrical contact with the peripheral surface of the porous material tip 630. Another possible Wenner arrangement has four parallel straight electrodes embedded in the porous material tip.

FIGS. 7A and 7B show another salinity sensor 720, designed to reduce hysteresis in the water content response of the sensor. In the embodiment of FIGS. 2 to 4, part of such hysteresis comes from air pressure that builds up in the tubular housing 24 due to air entrapment and constraining the convective flow of liquid in the porous material tip 30. The design of the salinity sensor 720 provides a larger contact surface between the porous material tip 730 and the porous medium to be sampled and avoid air entrapment causing hysteresis. More specifically, there is a contact surface on opposite faces 740, 742 of the porous material tip 730. The sensor 720 comprises the porous material tip 730, an electrical conductivity meter 754 having two electrodes 756, 758, and a head with an antenna (not shown) including the electrical circuitry similarly to the head and antenna of the embodiment of FIGS. 2 to 4. The porous material tip 730 electrically connects to the head through an electrical wire housing 724. In this case, the porous material tip 730 extends completely out of the housing 724. The housing 724 only engages to the porous material tip 730 on part of face 742. The two electrodes 756, 758 comprise a straight electrode 756 and a ring electrode 758. The straight electrode 756 penetrates in the porous material tip 730 from the housing 724 and in direction of the opposite face 740. The ring electrode 758 surrounds the porous material tip 730 radially relative to the straight electrode 756 and is in direct contact with the porous material tip 730. This configuration allows the liquid to be sampled to exchange with the material tip 730 from side to side of the porous material tip 730 and axially to the ring electrode 758.

It is noted that some hysteresis may arise from the fact that, due to gravity, it is more difficult for a liquid phase solution to fully refill the porous material tip from the bottom to the top than from the top to the bottom of the tip. Hysteresis may thus be reduced by allowing the liquid phase solution to reach the porous material tip from the top or from the side rather than from the bottom. Positioning the porous material tip horizontally in the porous medium may thus help in reducing hysteresis. It is thus noted that the configuration of the porous material tip and electrodes and the connection between the porous material tip and the head may vary such that the porous material tip is to be positioned in the porous medium to be sampled such that the straight electrode is either vertical or horizontal.

FIG. 8 shows a salinity sensor 820 similar to the one of FIGS. 2 to 4 but which is modular in that the head 832 is separate and independent from the sensing portion 830 which is to be inserted in the porous medium to be sampled. The head 832 has a plurality of connectors 840 for interchangeably connecting various types of sensing portions 830 such as salinity sensing portions but also humidity sensing portions, temperature or water potential sensing portions. A plurality of sensing portions may also be connected to the head 832 all together. The various sensing portions 830 are connected to the head 832 using flexible electrical connections 862 providing more flexibility in the positioning of the sensing portions 830 and allowing the porous material tip to be positioned horizontally in the porous medium.

The embodiments of the invention described above are intended to be exemplary only. The scope of the invention is therefore intended to be limited solely by the scope of the appended claims.

What is claimed is:

1. A sensor for measuring a concentration in a liquid solution in a porous medium, said sensor comprising:
   a porous material having pores with a substantially uniform pore size and wherein, when said porous material is at least partly inserted in said porous medium, said pores are substantially saturated with said liquid solution when said porous medium contains said liquid solution in a content above a threshold value and said pores are substantially empty from said liquid solution when said content is below said threshold value; and
   an electrical transducer for measuring an electrical quantity in said porous material, said electrical quantity being representative of said concentration in said liquid solution.

2. The sensor as claimed in claim 1, wherein said electrical transducer comprises at least one electrode in electrical contact with said porous material.

3. The sensor as claimed in claim 1, wherein said pore size is between 1 and 1000 micrometers.

4. The sensor as claimed in claim 1, wherein said porous medium is substantially free of plant available water below said threshold value and said porous medium contains plant available water above said threshold value.

5. The sensor as claimed in claim 1, wherein said electrical transducer comprises an electrical conductivity meter for measuring an electrical conductivity of said porous material.

6. The sensor as claimed in claim 5, wherein said porous material has substantially no electrical conductivity when said pores are empty and wherein said concentration is a concentration of salts in said liquid solution, said electrical conductivity of said porous material being representative of a salinity of said porous medium.

7. The sensor as claimed in claim 6, wherein a relationship between said electrical conductivity and said salinity has a predetermined temperature variation, said sensor further comprising a temperature measuring device for said electrical conductivity meter to compensate for said temperature variation.

8. The sensor as claimed in claim 5, wherein said electrical conductivity meter comprises a first and a second electrodes in electrical contact with said porous material and an electrical conductivity measurement circuit.

9. The sensor as claimed in claim 5, wherein said electrical conductivity meter comprises a straight electrode inserted into the porous material and a ring electrode in electrical contact with a peripheral surface of the porous material for measuring an electrical conductivity of said porous material.

10. The sensor as claimed in claim 5, wherein said electrical conductivity meter comprises four electrodes in a Wenner arrangement for measuring an electrical conductivity of said porous material.

11. The sensor as claimed in claim 1, wherein said electrical transducer comprises a selective electrode sensitive to a specific component in said liquid solution, said concentration being a concentration in said specific component in said liquid solution.

12. The sensor as claimed in claim 1, wherein said porous medium is a growing media for growing plants.

13. The sensor as claimed in claim 1, wherein said porous material has a first end surface and a second end surface substantially opposite to said first surface, said first end surface and said second end surface being at least partly in direct contact with said porous medium when said sensor is inserted in said porous medium.

14. A sensor for measuring a parameter in a liquid solution in a porous medium, said sensor comprising:
   a porous material tip to be at least partly inserted in said porous medium, said porous material tip having pores of substantially uniform size, said size being such that said porous material tip is to be substantially saturated in said liquid solution when said porous medium contains plant available water and such that said porous material tip is to be substantially free when said porous medium contains substantially no plant available water; and
   an electrical transducer for measuring an electrical quantity in said porous material tip, said electrical quantity being indicative of said parameter of said liquid solution.

15. The sensor as claimed in claim 14, wherein said size of said pores is between 1 and 1000 micrometers.

16. The sensor as claimed in claim 14, wherein said electrical transducer comprises at least one electrode in electrical contact with said porous material tip.

17. The sensor as claimed in claim 14, wherein said electrical transducer comprises an electrical conductivity meter for measuring an electrical conductivity in said liquid solution.

18. The sensor as claimed in claim 17, wherein said porous material tip has substantially no electrical conductivity when said pores are empty.

19. The sensor as claimed in claim 17, wherein a salinity of said liquid solution is a unique function of said electrical conductivity, thereby providing a salinity sensor and wherein a relationship between said electrical conductivity and said salinity has a predetermined temperature variation, said sensor further comprising a temperature measuring device for said electrical conductivity meter to compensate for said temperature variation.

20. The sensor as claimed in claim 17, wherein said electrical transducer comprises a selective electrode sensitive to specific component in said liquid solution, said parameter being a concentration in said specific component in said liquid solution.

21. A method for measuring a parameter in a porous medium using a porous material tip having pores having a pore size, said porous material tip to be inserted in said porous medium, said method comprising:

determining said pore size such that, when there is plant available water in said porous medium, pores are substantially saturated with said plant available water and such that, when said porous medium is substantially free of available water, said pores are free of said available water;

providing a porous material tip having substantially uniform pores of said pore size;

inserting said porous material tip in said porous medium;

measuring an electrical quantity in said porous material tip, said electrical quantity being indicative of said parameter; and     outputting a measurement of said parameter obtained from the measured electrical quantity.

22. The method as claimed in claim 21, wherein said electrical quantity is an electrical conductivity of said porous material tip.

23. The method as claimed in claim 22, wherein said parameter is a salinity of said porous material tip, said electrical conductivity.

24. The method as claimed in claim 21, wherein said parameter is a concentration of a specific component in plant available water.

* * * * *